United States Patent [19]

Kleemann et al.

[11] Patent Number: 4,716,247

[45] Date of Patent: Dec. 29, 1987

[54] PROCESS FOR THE PRODUCTION OF THIOSEMICARBAZIDE

[75] Inventors: Axel Kleemann; Herbert Klenk; Wolfgang Schulz, all of Hanau, Fed. Rep. of Germany

[73] Assignee: Degussa Aktiengesellschaft, Frankfurt am Main, Fed. Rep. of Germany

[21] Appl. No.: 462,973

[22] Filed: Feb. 1, 1983

[30] Foreign Application Priority Data

Feb. 6, 1982 [DE] Fed. Rep. of Germany ....... 3204149

[51] Int. Cl.[4] .................. C07C 159/00; C01B 21/093; C01C 3/20
[52] U.S. Cl. ........................................ 564/18; 423/366
[58] Field of Search ........................... 564/18; 423/366

[56] References Cited

U.S. PATENT DOCUMENTS

| | | | |
|---|---|---|---|
| 570,480 | 11/1896 | Hood et al. | 423/366 |
| 862,678 | 8/1907 | Tcherniac | 423/366 |
| 2,657,234 | 10/1953 | Klarer et al. | 564/18 |
| 2,710,243 | 6/1955 | Swimmer | 423/366 |
| 2,731,496 | 1/1956 | Taylor | 564/18 |
| 2,771,489 | 11/1956 | Audrieth et al. | 564/18 |
| 2,806,880 | 9/1957 | Kippur | 564/18 |
| 3,009,955 | 11/1961 | Rieche et al. | 564/18 |
| 3,459,498 | 8/1969 | Johnson | 423/366 |
| 4,237,066 | 12/1980 | Barton | 564/18 |
| 4,256,661 | 3/1981 | Barton et al. | 564/18 |

FOREIGN PATENT DOCUMENTS 1274574 8/1968 Fed. Rep. of Germany .
118133 6/1968 United Kingdom .

OTHER PUBLICATIONS

Richter, *Textbook of Organic Chemistry*, p. 265, Wiley & Sons, Inc. N.Y. (1938).
Kleemann et al., European Patent 0 085 887, Aug. 1983.

*Primary Examiner*—Charles F. Warren
*Assistant Examiner*—Carolyn S. Greason
*Attorney, Agent, or Firm*—Cushman, Darby & Cushman

[57] ABSTRACT

To produce thiosemicarbazide hydrazine is reacted with hydrogen cyanide and sulfur to form hydrazine thiocyanate, and this is then converted into the thiosemicarbazide at an elevated temperature. Advantageously, the reaction is carried out in a polar solvent.

13 Claims, No Drawings

PROCESS FOR THE PRODUCTION OF THIOSEMICARBAZIDE

BACKGROUND OF THE INVENTION

The invention is directed to a process for the production of thiosemicarbazide by formation of hydrazine thiocyanate and converting this into the thiosemicarbazide.

It is known that hydrazine thiocyanate is formed if a salt of thiocyanic acid is brought together with hydrazine or a salt of hydrazine in aqueous medium and that the hydrazine thiocyanate is converted into thiosemicarbazide at a higher temperature. For example, ammonium thiocyanate is mixed with hydrazine, water, and an alkanol having 3 to 5 carbon atoms and this mixture heated to boiling after addition of catalytic amounts of acetone (Great Britain patent No. 1118133) or ammonium thiocyanate and hydrazine sulfate are dissolved in water, and this solution is heated to boiling after addition of catalytic amounts of acetaldehyde (German Pat. No. 1274574). A disadvantage of the known processes is that equivalent amounts of byproducts, for example, ammonia or ammonium sulfate, form, and these byproducts can either not be recovered and used or at all events they can only by recovered and used at considerable expense.

SUMMARY OF THE INVENTION

There has now been found a process for the production of thiosemicarbazide by formation of hydrazine thiocyanate and its conversion into thiosemicarbazide characterized by reacting hydrazine with hydrogen cyanide and sulfur to form hydrazine thiocyanate. The hydrazine thiocyanate is then converted into thiosemicarbazide at higher temperature. In this process, the thiosemicarbazide is formed in excellent yield. Especial advantages of the process are that it is started directly from the simple materials sulfur and hydrogen cyanide, and there is eliminated the necessary accumulation of equivalent amounts of byproducts of the known process.

To carry out the process of the invention, the hydrazine is reacted with the hydrogen cyanide and sulfur, suitably in the presence of an organic solvent. As solvents, there can be used with advantage polar solvents, which, however, are otherwise inert. This type of solvent, for example, includes alcohols or ethers. Preferably, there are used alkanols, which in a given case are substituted (i.e., with an inert substituent), especially alkanols having 1 to 4 carbon atoms, e.g., methanol, ethanol, n-propanol, isopropanol, n-butanol, t-butanol, and sec-butanol and cyclic ethers, e.g., tetrahydrofuran, and especially dioxane. The proportions of hydrazine to solvent depend to a certain extent on the type of solvent. Generally, it is advantageous to use at least about two parts by weight of solvent for each part by weight of hydrazine.

The reaction can also take place in the presence of water, but generally it is advantageous that there be present at least one part by weight of organic solvent per part by weight of water. Preferably there are used at least ten parts by weight of organic solvent for each part by weight of water.

The hydrazine and the hydrogen cyanide are employed as such or as solutions, the sulfur is employed as such or as a suspension, suitably in one of the solvents mentioned. Preferably, the hydrazine is used as hydrazine hydrate. For example, sulfur is present as a suspension, and there is fed into this suspension hydrazine and hydrogen cyanide, or a solution of hydrazine cyanide is prepared by addition of hydrogen cyanide to a solution of hydrazine, and there is introduced sulfur into the solution of hydrazine cyanide.

Although the ratio of hydrazine to sulfur as well as the ratio of hydrogen cyanide to sulfur can be chosen substantially at pleasure, it is generally suitable not to deviate substantially from stoichiometry. With advantage, there is used about 1.0 to 1.2 moles of hydrazine and about 1.0 to 1.2 moles of hydrogen cyanide, better 1.0 to 1.1 moles of hydrazine and 1.0 to 1.1 moles of hydrogen cyanide per gram atom of sulfur. Especially suited are amounts equivalent to each other of hydrazine, hyrogen cyanide, and sulfur.

The reaction temperature in a given case depends on the molar ratios and the type of solvent. Generally, temperatures are used between about 0° and 60° C. Preferred are temperatures between 0° and 30° C. The pressure can be chosen substantially at random. However, it is advantageous not to deviate substantially from normal pressure (1 bar).

The hydrazine thiocyanate is recovered from the reaction mixture, for example, by driving off the solvent, in a given case under reduced pressure. For the purpose of conversion into thiosemicarbazide, the hydrazine thiocyanate is treated in known manner at elevated temperature. Preferably for this purpose, it is dissolved in water or in an organic solvent, especially in one of the above-mentioned polar solvents or in a mixture of an organic solvent with water, and there is added, if necessary, as catalyst an aldehyde or a ketone, especially acetone.

Generally, for the purpose of convertion into thiosemicarbazide, the treatment of hydrazine thiocyanate is carried out at a temperature between about 90° and 130° C., preferably between 95° and 110° C. Although hereby the pressure can be chosen substantially at pleasure, it is advantageous not to deviate substantially from normal pressure (1 bar). In many cases, because of the presence of volatile materials, it is necessary to select a higher pressure corresponding to the temperature.

A particularly preferred procedure is to treat the reaction mixture resulting from the reaction of the hydrazine with the hydrogen cyanide and sulfur directly for the conversion of the hydrazine thiocyanate into thiosemicarbazide at the elevated temperature. In this case, the mother liquor remaining after the separation of the thiosemicarbazide can be used repeatedly for further charges as solvent.

The process can comprise, consist essentially of, or consist of the stated steps with the recited materials.

DETAILED DESCRIPTION

EXAMPLE 1

To a solution of 25 grams (0.5 mole) of hydrazine hydrate in 30 ml of dioxane there was first added dropwise a solution of 13.5 grams (0.5 mole) of hydrogen cyanide in 80 ml of dioxane and then 16 grams (0.5 gram atom) of sulfur. The temperature of the mixture meanwhile and for a further 15 minutes was held at 10° C. and subsequently held for 8 hours at 90° C. Thiosemicarbazide separated off in the cooling. The melting point of the material was 172° C. The yield amounted to 25 grams, corresponding to 55%, based on the sulfur employed. The mother liquor remaining after the separation of the thiosemicarbazide was used for another charge as solvent. In this charge the yield was 32 grams, corresponding to 79% based on the sulfur employed.

EXAMPLE 2(a)

To a solution of 25 grams (0.5 mole) of hydrazine hydrate in 30 ml of methanol, there was first added dropwise a solution of 13.5 grams (0.5 mole) of hydrogen cyanide in 80 ml of methanol and then 16 grams (0.5 gram atom) of sulfur. The temperature of the mixture during this time and for a further 10 minutes was held at 5° C. Then the mixture was evaporated to dryness at 10 mbar. The hydrazine thiocyanate remaining as a residue thereby was taken up in 120 ml of xylene. The mixture of 0.5 bar 8 hours was held at 110° C. In the cooling thiosemicarbazide separated off. This was recrystallized in water. The melting point of the material was 174° C. The yield was 29 grams, corresponding to 72% based on the sulfur employed.

EXAMPLE 2(b)

The procedure was as in Example 2(a), but the hydrazine thiocyanate remaining as a residue in the evaporation was not taken up in xylene but in 130 ml of water. After addition of 0.5 ml of acetone, the mixture was held for 5 hours at 97° C. The melting point of the thiosemicarbazide was 171° C. The yield was 28 grams, corresponding to 69%, based on the sulfur employed. The mother liquor which accumulated in the separation of the thiosemicarbazide was used in a further similar charge for dissolving of the hydrazine thiocyanate which remained as a residue in the evaporation. In this charge, the yield was 37 grams, corresponding to 91%, based on the sulfur employed.

EXAMPLE 3

There were simultaneously fed into a suspension of 32.0 grams (1.0 gram atom) of sulfur in 280 ml of n-butanol 29.7 grams (1.1 moles) of hydrogen cyanide and 55 grams (1.1 mole) of hydrazine hydrate. Meanwhile, the temperature was held at 10° C. and further held after the addition of 2 ml acetone and 2 mol of 40% sulfuric acid for 4 hours at 95° to 105° C. Hereby the water was driven off as an azeotrope. Thiosemicarbazide separated off in the cooling. Its melting point was 179° C. The yield was 67 grams, corresponding to 74%, based on the sulfur employed. For three subsequent similar charges the mother liquor remaining in the preceding charge after the separation of the thiosemicarbazide was used as solvent. The yield in these charges averaged 75 grams, corresponding to 83%. The melting point of the thiosemicarbazide in each case was 179° C.

The entire disclosure of German priority application No. P 3204149.7 is hereby incorporated by reference.

What is claimed is:

1. A process for forming hydrazine thiocyanate comprising reacting hydrazine with hydrogen cyanide and sulfur.

2. A process according to claim 1 wherein there are employed 1.0 to 1.2 moles of hydrazine and about 1.0 to 1.2 moles of hydrogen cyanide per gram atom of sulfur.

3. A process of preparing thiosemicarbazide comprising reacting hydrazine with hydrogen cyanide and sulfur to form hydrazine thiocyanate and heating the hydrazine thiocyanate to form thiosemicarbazide.

4. A process according to claim 3 carried out in an inert polar solvent.

5. A process according to claim 4 wherein the solvent is an alcohol or an ether.

6. A process according to claim 5 wherein the solvent is an alkanol having 1 to 4 carbon atoms, tetrahydrofurane or dioxane.

7. A process according to claim 3 wherein there are employed 1.0 to 1.2 moles of hydrazine and about 1.0 to 1.2 moles of hydrogen cyanide per gram atom of sulfur.

8. A process according to claim 7 wherein there are used 1.0 to 1.1 moles of hydrazine and 1.0 to 1.1 moles of hydrogen cyanide per gram atom of sulfur.

9. A process according to claim 4 including the steps of separating the thiosemicarbazide formed from the mother liquor and recycling the mother liquor as solvent for the further reaction of hydrazine, with hydrogen cyanide and sulfur.

10. A process according to claim 4 wherein the hydrazine thiocyanate is heated at 90° to 130° C. to form the thiosemicarbazide.

11. A process according to claim 10 wherein the temperature is 95° to 110° C.

12. A process according to claim 4 comprising heating the hydrazine thiocyanate formed without separation of solvent directly to form the thiosemicarbazide and recovering the thiosemicarbazide.

13. A process according to claim 4 comprising separating the hydrazine thiocyanate formed from the solvent, taking up the separated hydrazine thiocyanate in an inert polar solvent and heating the solution to form thiosemicarbazide and recovering the thiosemicarbazide.

* * * * *